US012751813B2

(12) United States Patent
Muller et al.

(10) Patent No.: US 12,751,813 B2
(45) Date of Patent: Oct. 6, 2026

(54) CORNEAL IMPLANT SYSTEMS AND METHODS

(71) Applicant: ALLOTEX, INC., Boston, MA (US)

(72) Inventors: David Muller, Boston, MA (US); Michael Mrochen, Eglisau (CH)

(73) Assignee: ALLOTEX, INC., Boston, MA (US)

(*) Notice: Subject to any disclaimer, the term of this patent is extended or adjusted under 35 U.S.C. 154(b) by 0 days.

(21) Appl. No.: 18/197,808

(22) Filed: May 16, 2023

(65) Prior Publication Data

US 2023/0277300 A1 Sep. 7, 2023

Related U.S. Application Data

(63) Continuation of application No. 16/219,894, filed on Dec. 13, 2018, now Pat. No. 11,690,706.

(Continued)

(51) Int. Cl.
*A61F 9/008* (2006.01)
*A61B 90/00* (2016.01)

(Continued)

(52) U.S. Cl.
CPC ............ *A61F 2/142* (2013.01); *A61F 2/0095* (2013.01); *A61F 2/145* (2013.01); *A61F 9/008* (2013.01);

(Continued)

(58) Field of Classification Search
None
See application file for complete search history.

(56) References Cited

U.S. PATENT DOCUMENTS 4,860,885 A 8/1989 Kaufman et al.
6,280,449 B1 8/2001 Blake (Continued)

FOREIGN PATENT DOCUMENTS

EP 2526896 10/2015
EP 1989585 8/2016

(Continued)

OTHER PUBLICATIONS

"Jay, et al., Characterization of tissue-engineered posterior corneas using second- and third-harmonic generation microscopy, 2015, PLOS One, pp. 1-13" (Year: 2015).*

(Continued)

*Primary Examiner* — Michael T. Holtzclaw
(74) *Attorney, Agent, or Firm* — McDonnell Boehnen Hulbert & Berghoff LLP

(57) ABSTRACT

A storage/delivery device includes a first wall defining a well configured to receive a corneal tissue. The storage/delivery device includes a second wall configured to be positioned over the first wall and to seal the well. The second wall includes a recess configured to extend into the well to define a chamber between the first wall and the second wall. The chamber is configured to hold the corneal tissue when the second wall seals the well. A system may include the storage/delivery device above and a measurement system configured to measure the corneal tissue disposed in the well. In one example embodiment, the measurement system is an optical coherence tomography (OCT) system. In another example embodiment, the measurement system is a second-harmonic generation (SHG) or third-harmonic generation (THG) microscopy system.

20 Claims, 5 Drawing Sheets

Related U.S. Application Data

(60) Provisional application No. 62/598,099, filed on Dec. 13, 2017.

(51) Int. Cl.
*A61F 2/00* (2006.01)
*A61F 2/14* (2006.01)

(52) U.S. Cl.
CPC .. *A61F 9/00831* (2013.01); *A61B 2090/3735* (2016.02); *A61F 2009/00851* (2013.01); *A61F 2009/00872* (2013.01); *A61F 2240/001* (2013.01); *A61L 2430/16* (2013.01)

(56) References Cited

U.S. PATENT DOCUMENTS

| | | | | |
|---|---|---|---|---|
| 6,540,358 | B2 | 4/2003 | Otten, III | |
| 6,581,993 | B2 | 6/2003 | Nigam et al. | |
| 7,662,611 | B2 | 2/2010 | Schmidt et al. | |
| 8,057,541 | B2 | 11/2011 | Dishler et al. | |
| 8,900,296 | B2 | 12/2014 | Holiday | |
| 9,101,465 | B2 | 8/2015 | Berner et al. | |
| 9,603,700 | B2 | 3/2017 | Berner | |
| 9,877,823 | B2 | 1/2018 | Schneider et al. | |
| 10,092,393 | B2 | 10/2018 | Muller | |
| 10,449,090 | B2 | 10/2019 | Muller | |
| 10,555,805 | B2 | 2/2020 | Lang | |
| 10,583,041 | B2 | 3/2020 | Holliday | |
| 10,835,371 | B2 | 11/2020 | Dishler et al. | |
| 10,952,900 | B2 | 3/2021 | Muller | |
| 2003/0045930 | A1 | 3/2003 | Nguyen | |
| 2009/0326650 | A1 | 12/2009 | Zickler et al. | |
| 2011/0008877 | A1 * | 1/2011 | Skelnik | A61F 2/0095 435/284.1 |
| 2013/0123916 | A1 | 5/2013 | Nigam et al. | |
| 2013/0130222 | A1 | 5/2013 | Ruzza et al. | |
| 2014/0264980 | A1 | 9/2014 | Muller | |
| 2014/0368793 | A1 | 12/2014 | Friedman et al. | |
| 2015/0133901 | A1 | 5/2015 | Serdarevic et al. | |
| 2016/0029618 | A1 * | 2/2016 | Gain | A01N 1/146 435/284.1 |
| 2019/0350193 | A1 * | 11/2019 | Gharbi | A01N 1/143 |
| 2020/0253720 | A1 | 8/2020 | Muller et al. | |

FOREIGN PATENT DOCUMENTS

| | | | |
|---|---|---|---|
| EP | 2858612 | B1 | 1/2017 |
| EP | 2509536 | | 2/2017 |
| EP | 2664300 | | 10/2020 |
| WO | 2014/152882 | A1 | 9/2014 |

OTHER PUBLICATIONS

Ubels et al., “A redesigned corneal holder for bovine cornea opacity and permeability assay that maintains normal corneal morphology”, Toxicology in Vitro, vol. 16, pp. 6221-6628 (2002) (Year: 2002).

* cited by examiner

CORNEAL IMPLANT SYSTEMS AND METHODS

CROSS-REFERENCE TO RELATED APPLICATIONS

This application is a continuation of U.S. patent application Ser. No. 16/219,894, filed Dec. 13, 2018, which claims priority to, and benefit of, U.S. Provisional Patent Application Ser. No. 62/598,099, filed Dec. 13, 2017, the contents of which are incorporated entirely herein by reference.

FIELD OF THE INVENTION

The present disclosure relates generally to systems and methods for correcting vision, and more particularly, to systems and methods relating to implants to reshape the cornea in order to correct vision.

BACKGROUND

A variety of eye disorders, such as myopia, hyperopia, astigmatism, and presbyopia, involve abnormal shaping of the cornea. This abnormal shaping prevents the cornea from properly focusing light onto the retina in the back of the eye (i.e., refractive error). A number of treatments attempt to reshape the cornea so that the light is properly focused. For instance, a common type of corrective treatment is LASIK (laser-assisted in situ keratomileusis), which employs a laser to reshape the cornea surgically.

SUMMARY

According to aspects of the present disclosure, embodiments provide implants for reshaping the cornea in order to correct vision. For instance, such implants may address the refractive errors associated with eye disorders such as myopia, hyperopia, astigmatism, and presbyopia. The implants may be formed from natural tissue, such as donor corneal tissue.

According to aspects of the present disclosure, a storage/delivery device includes a first wall defining a well configured to receive a corneal tissue. The storage/delivery device includes a second wall configured to be positioned over the first wall and to seal the well. The second wall includes a recess configured to extend into the well to define a chamber between the first wall and the second wall. The chamber is configured to hold the corneal tissue when the second wall seals the well.

According to other aspects of the present disclosure, a system includes the storage/delivery device above and a measurement system configured to measure the corneal tissue disposed in the well. In one embodiment, the measurement system is an optical coherence tomography (OCT) system, where the OCT system is positioned to direct incident light to the corneal tissue in the well and to receive optical scattering from the corneal tissue in response to the incident light, the optical scattering indicating a measurement of the corneal tissue. In another embodiment, the measurement system is a second-harmonic generation (SHG) or third-harmonic generation (THG) microscopy system, the SHG or THG microscopy system including: a light source positioned to direct incident light to the corneal tissue; and a detector positioned to receive a respective 2nd or 3rd harmonic light respectively from the corneal tissue in response to the incident light, the respective 2nd or 3rd harmonic light indicating a measurement of the corneal tissue, where the light source and the detector are positioned on opposite sides of the first wall and the first wall is transmissive to allow the detector to receive the respective 2nd or 3rd harmonic light.

According to further aspects of the present disclosure, a method for processing corneal tissue includes receiving a corneal tissue and placing the corneal tissue in a well defined by a first wall. The method also includes filling the well with a fluid medium to keep the corneal tissue hydrated in the well. Additionally, the method includes sealing the corneal tissue and the fluid medium in the well by positioning a second wall over the first wall and coupling the second wall to the first wall. The second wall includes a recess configured to extend into the well to define a chamber between the first wall and the second wall, the chamber configured to hold the corneal tissue when the well is sealed.

DESCRIPTION

Example systems and methods employ implants to reshape the cornea in order to correct vision. For instance, such embodiments may address the refractive errors associated with eye disorders such as myopia, hyperopia, astigmatism, and presbyopia. Example systems and methods employ implants that are formed from natural tissue, such as donor corneal tissue.

Implants formed from donor cornea can be employed to reshape the cornea in order to correct a variety of eye disorders, such as myopia, hyperopia, astigmatism, and presbyopia. Approaches for producing and implementing such implants are described, for instance, in U.S. Patent Application Publication No. 2014/0264980, filed Jan. 10, 2014, U.S. Patent Application Publication No. 2017/0027754, filed Feb. 28, 2016, and U.S. Patent Application Publication No. 2017/0319329, filed May 5, 2017, the contents of these applications being incorporated entirely herein by reference.

An implant can be formed by shaping a lenticule that is cut from a donor cornea. In some cases, the single donor cornea is cut to maximize the number of lenticules, thereby maximizing the number of implants from the single donor cornea. According to one approach, the lenticule may be prepared and packaged (e.g., by a supplier) for delivery and subsequent reshaping (e.g., by a practitioner) at or near the time of actual implantation into the cornea. As such, the lenticule may provide a more general shape (e.g., a blank) that can be subsequently reshaped into an implant according to any specific shape. The specific shape may cause a change in refractive power when implanted. In addition, the shape may include desired edge characteristics and other features that allow the structure of the implant to blend or transition smoothly into the surrounding eye structure, for instance, to improve optics and/or promote epithelial growth over the implant.

If a separate supplier packages and delivers a lenticule as a blank to a practitioner, the practitioner may need to know the starting measurements of the lenticule so that the proper amount of tissue can be accurately removed from the lenticule to obtain a precisely shaped corneal implant. The supplier may take the measurements of the lenticule and may provide the measurements to the practitioner.

Embodiments provide a storage/delivery device (e.g., container) for holding a lenticule for delivery to a practitioner. Advantageously, the storage/delivery device allows the lenticule to maintain its shape and holds a fluid medium to maintain hydration for the lenticule during delivery. Furthermore, the storage/delivery device allows optical measurement techniques to be applied to the lenticule while it is in the device.

Figure 1:
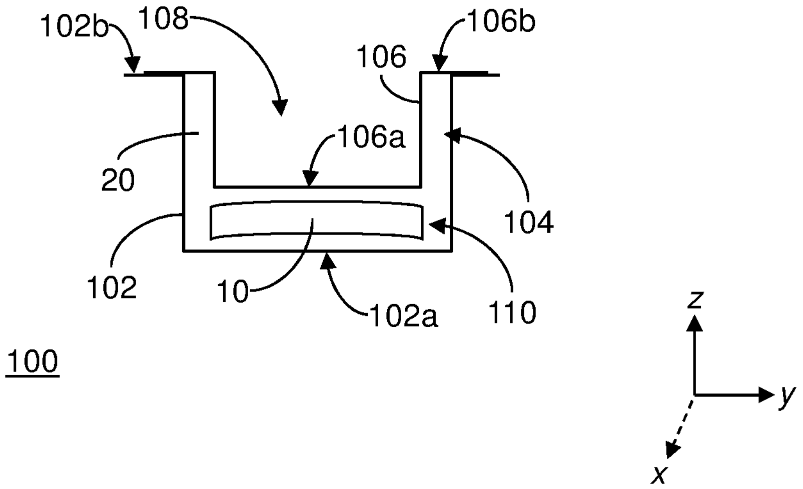
FIG. 1 illustrates an example storage/delivery device for holding corneal tissue, according to aspects of the present disclosure.

FIG. 1 illustrates an example storage/delivery device 100 for holding a lenticule 10. Aspects of the storage/delivery device 100, for instance, may be formed from glass, plastic, or similarly suitable material. The storage/delivery device 100 includes a first wall 102 that defines a well 104 that is configured to receive the lenticule 10. The well 104 can be filled with a medium 20, including albumin for instance, to keep the lenticule 10 hydrated in the well 104. The lenticule 10 may have a diameter in the x-y plane of up to approximately 10 mm, but more typically a diameter of approximately 3 mm to approximately 7 mm. In addition, the lenticule 10 may have a thickness along the z-axis of approximately 10 μm to approximately 50 μm. (FIG. 1 provides a simplified illustration of the storage/delivery device 100 and the lenticule 10; the storage/delivery device 100 and the lenticule 10 as shown in FIG. 1 are not to-scale.) Although the lenticule 10 may have a generally circular profile in the x-y plane, the lenticule 10 may have other shapes and dimensions.

The first wall 102 includes a bottom portion 102*a* that defines the bottom of the well 104. When the lenticule 10 is received into the well 104, the lenticule 10 is situated along the bottom portion 102*a*. In some embodiments, the portion 102*a* may be contoured or otherwise shaped to accommodate the lenticule 10 and keep the lenticule 10 in place. For instance, the bottom portion 102*a* may define a depression that receives the lenticule 10.

The storage/delivery device 100 also includes a second wall 106 that is configured to be positioned over the first wall 102 and to seal the well 104. In particular, the second wall 106 defines a recess 108 that can extend into the well 104 to define a chamber 110 between the first wall 102 and the second wall 106. The lenticule 10 and the medium 20 are sealed within the chamber 110. The first wall 102 includes a top portion 102*b* that defines a periphery at the top of the well 104. The second wall 106 includes a top portion 106*b* that defines a periphery at the top of the recess 108. Once the lenticule 10 and the medium 20 are placed in the well 104, the second wall 106 is placed over the first wall 102 with the recess 108 extending into the well 104. The top portion 106*b* of the second wall 106 can then be coupled to the top portion 102*b* of the first wall 102 to seal the well 104 and form the chamber 110. The coupling can be achieved, for instance, with an adhesive, mechanical coupling (e.g., threaded coupling, fasteners, clips, etc.), or other similarly suitable approach.

The second wall 106 includes a bottom portion 106*a* that defines the bottom of the recess 108. When the second wall 106 seals the well 104, the lenticule 10 is positioned between the bottom portion 102*a* of the first wall 102 and the bottom portion 106*a* of the second wall 106. To accommodate the lenticule 10 and to keep the lenticule 10 in place, the distance along the z-axis between the bottom portions 102*a*, 106*a* may be approximately 100 μm (though other suitable dimensions are possible). Additionally, the diameter in the x-y plane of the bottom portion 106*a* may be approximately equal to the diameter of the lenticule 10. In some embodiments, the bottom portion 106*a* of the second wall 106 may also be contoured or otherwise shaped to keep the lenticule 10 in place. When positioned between the bottom portions 102*a*, 106*a*, the lenticule 10 can maintain its desired shape. For instance, the lenticule 10 can avoid rolling up or experiencing external forces that might affect its shape.

The example storage/delivery device 100, for instance, provides significant advantages over an approach that holds a lenticule in a plastic pouch. In a plastic pouch, it might be difficult to determine, identify, and locate the lenticule relative to the pouch, and the lenticule might also be susceptible to undesired changes in shape, e.g., due to squeezing of the pouch. In contrast, the lenticule 10 can be easily located within the well 104 of the storage/delivery device 100, and the storage/delivery device 100 allows the lenticule 10 to maintain the desired shape.

After the lenticule 10 is cut from the donor cornea (e.g., with a keratome, cryo-microtome, etc.), further preparation may include sterilizing the lenticule 10, shaping aspects of the lenticule 10 with a laser, and/or measuring the lenticule 10. The storage/delivery device 100 may be implemented at any point during the preparation process. According to an example implementation, after the lenticule 10 is cut from the donor cornea, the lenticule 10 may be placed in the well 104 of the storage/delivery device 100 (while in a humidified chamber) where it can be further shaped with a laser. While the lenticule 10 remains in the well 104, dimensions and/or other characteristics of the lenticule 10 can be measured and the lenticule 10 can be sterilized. The well 104 may then be filled with a fluid medium, including such as albumin, prior to sealing the well with the second wall 106. Other additional or alternative implementations and/or steps may be employed. For instance, in alternative implementations, the lenticule 10 might not undergo any further shaping with a laser while in the well 104. In yet other implementations, the sterilization may occur after the well 104 is filled with the fluid.

In some embodiments, the lenticule 10 may adhere to a surface of the storage/delivery device 100, e.g., the bottom portion 102*a* of the first wall 102. When the lenticule 10 adheres to such a surface, it can maintain the desired shape and remain in place for shaping with a laser, measurements, and/or other operations or manipulations. In some implementations, a pressure may be applied to the lenticule 10, e.g., with a fluid or a device, to cause it to adhere to the surface when in the well 104. As discussed above, aspects of the storage/delivery device 100 may be contoured to accommodate the lenticule 10; such contours may also help the lenticule 10 to adhere to a surface.

The dimensions and/or other characteristics of the lenticule 10 can be measured by employing optical techniques, such as optical coherence tomography (OCT), second-harmonic generation (SHG) microscopy, or third-harmonic generation (THG) microscopy. OCT involves low-coherence interferometry using light of relatively long wavelengths (e.g., near-infrared light) to capture micrometer-resolution, three-dimensional images based on the optical scattering by the corneal tissue. SHG or THG microscopy involves detecting, with a microscope, variations in optical density, path length, refractive index, etc., in the corneal tissue based on variations in the corneal tissue's ability to generate second- or third-harmonic light from incident light (i.e., light having half or one-third the incident wavelength), respectively.

Figure 2:
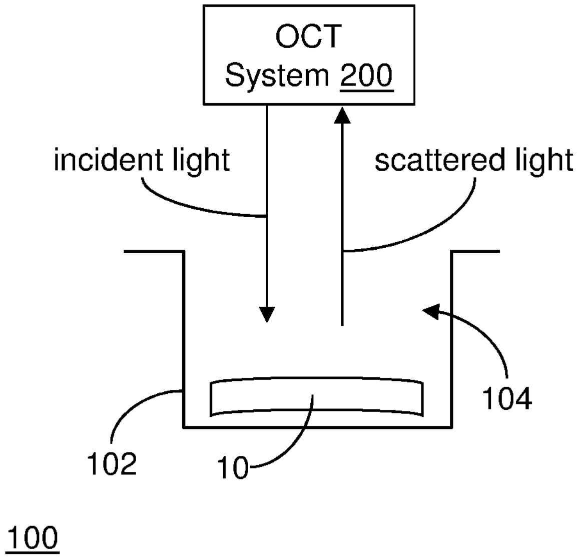
FIG. 2 illustrates the use of an example optical coherence tomography (OCT) system to measure corneal tissue disposed in a storage/delivery device, according to aspects of the present disclosure.

FIG. 2 illustrates the use of an example OCT system 200 to measure the lenticule 10 disposed in the well 104. In particular, the OCT system 200 is positioned to direct incident light (e.g., near-infrared light) to the lenticule 10 and to receive optical scattering (e.g., reflection) from the lenticule 10 in response to the incident light.

Figure 3:
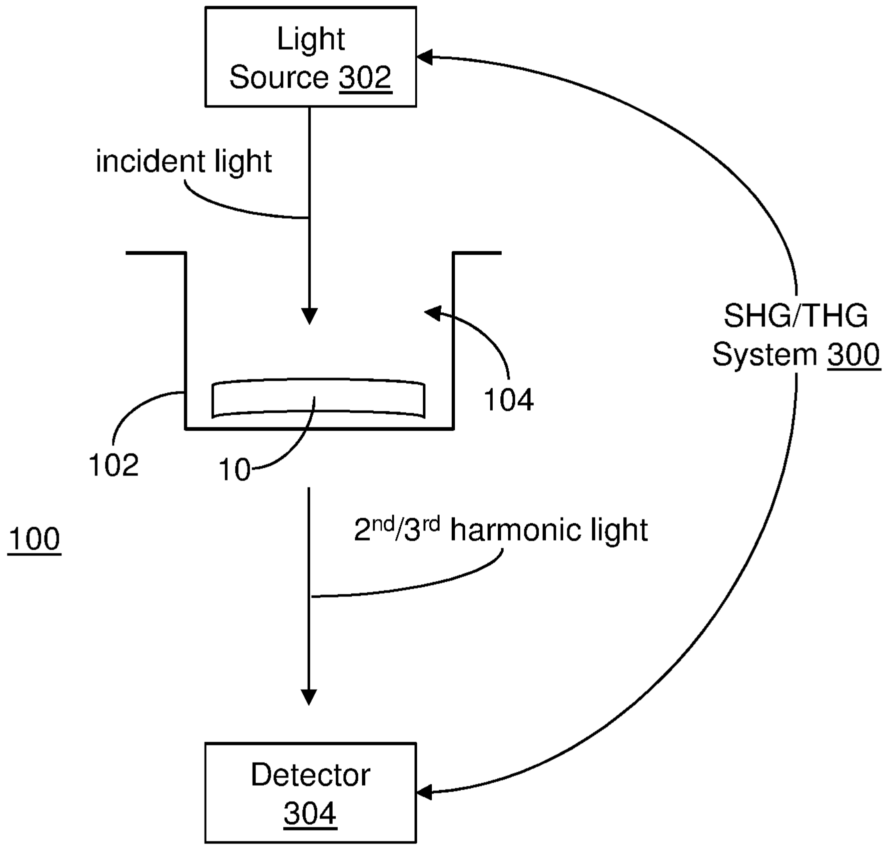
FIG. 3 illustrates the use of an example second-harmonic generation (SHG) or third-harmonic generation (THG) microscopy system to measure corneal tissue disposed in a storage/delivery device, according to aspects of the present disclosure.

FIG. 3 illustrates the use of an example SHG/THG microscopy system 300 to measure the lenticule 10 disposed in the well 104. In particular, the SHG/THG microscopy system 300 includes a light source 302 that is positioned to direct incident light to the lenticule 10. The SHG/THG microscopy system 300 also includes a detector 304 positioned to receive the $2^{nd}/3^{rd}$ harmonic light from the lenticule 10 in response to the incident light. As shown in FIG. 3, the light source 302 and the detector 304 are positioned on opposite sides of the first wall 102. As such, aspects of the first wall 102 are transmissive to allow the detector 304 to receive the $2^{nd}/3^{rd}$ harmonic light.

Although FIGS. 2 and 3 illustrate specific optical measurement techniques, the storage/delivery device 100 may be employed with any suitable optical or non-optical measurement system.

In general, tissue from donor cornea may experience swelling when placed in a fluid medium. While a volume of corneal tissue remains in an eye of a living donor, the volume of corneal tissue experiences physiological hydration conditions and maintains an initial size. When the volume of corneal tissue is removed from the living donor and stored in a fluid medium, however, the volume of corneal tissue experiences different hydration conditions. Thus, when stored in the medium, the volume of corneal tissue may swell from its initial size, resulting for instance in an increase in thickness. When the volume of corneal tissue is removed from the medium and placed in the physiological hydration conditions of a living recipient, the volume of corneal tissue shrinks from the swollen size back to its initial size. This phenomenon is referred hereinafter as deswelling. The corneal tissue shrinks by substantially the same factor by which it swells in the medium.

When forming an implant from a donor cornea, embodiments according to the present disclosure can account for the swelling that the corneal tissue experiences when stored in in a medium and the deswelling that the corneal tissue experiences when implanted into a living recipient. For instance, if a corneal implant of thickness 50 μm is needed in the living recipient, corneal tissue that has swelled in a medium can be cut into an implant with a thickness that is greater than 50 μm to accommodate anticipated deswelling. In particular, if the corneal tissue swells by a factor of two in the medium, the corneal tissue may be cut into an implant with a thickness of 100 μm, so that when deswelling occurs, the implant attains the desired thickness of 50 μm in the living recipient.

Figure 4:
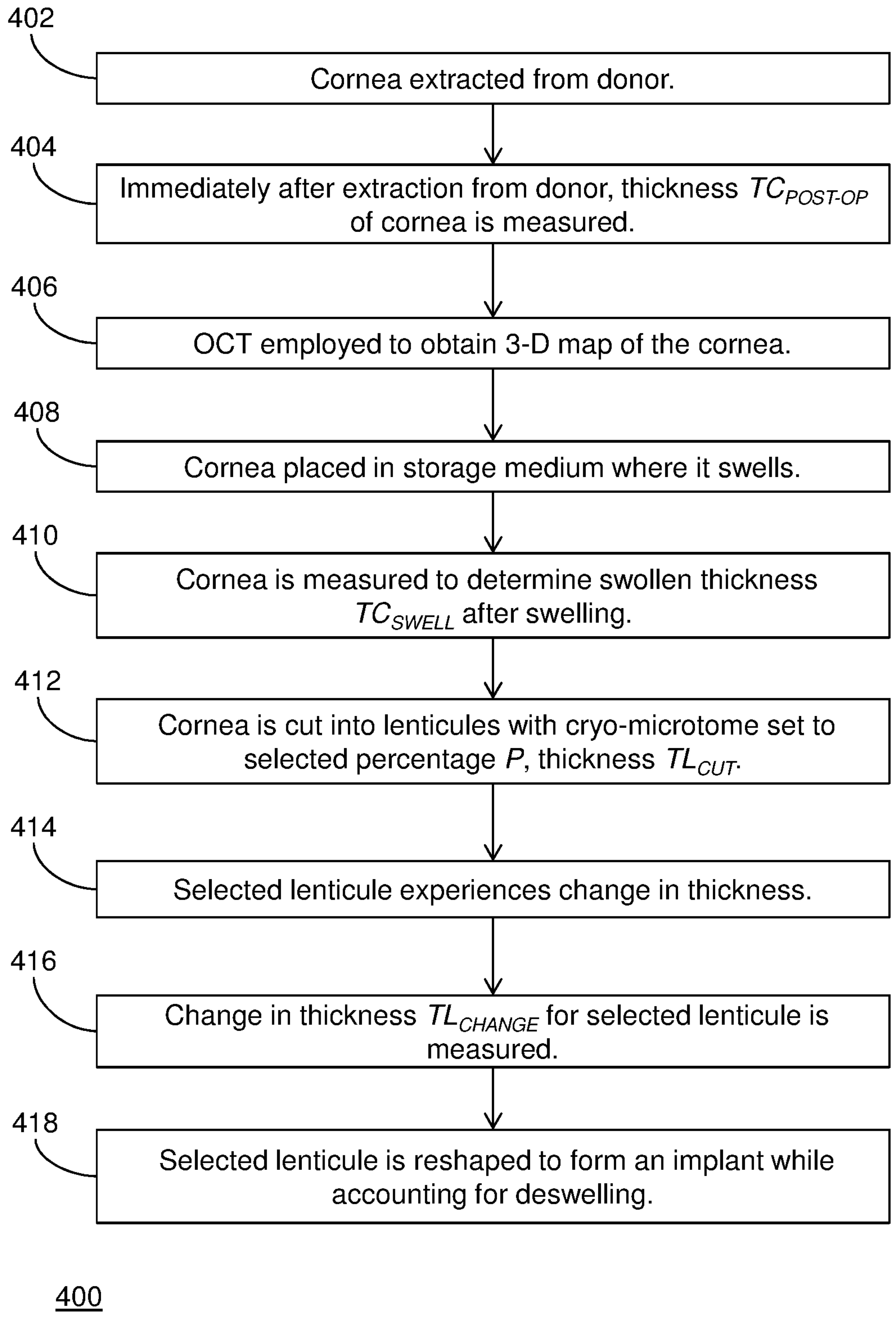
FIG. 4 illustrates an example approach for producing implants, where the approach accounts for swelling and deswelling of corneal tissue, according to aspects of the present disclosure.

FIG. 4 illustrates an example approach 400 for producing implants, where the approach 400 accounts for swelling and deswelling of corneal tissue. In act 402, a cornea is extracted from a donor in an operation. Immediately after the cornea is extracted from the donor, a post-operation thickness $TC_{POST\text{-}OP}$ of the cornea is measured in act 404. The thickness $TC_{POST\text{-}OP}$ provides a good approximation of the thickness of the cornea while still residing in the donor (i.e., prior to act 402). In act 406, OCT is employed to obtain a three-dimensional map of the cornea, which can be used for further processing of the corneal tissue. In act 408, the cornea is placed in a medium in a pouch where it swells. When the cornea is received in the pouch for further processing, a swollen thickness $TC_{SWELL}$ for the cornea is measured in act 410. The swollen thickness $TC_{SWELL}$ reflects the amount of swelling resulting from act 408.

In act 412, the cornea is cut into lenticules with a cryo-microtome or similar cutting device. Aspects of implementing a cryo-microtome are described, for instance, in U.S. Patent Application Publication No. 2017/0319329. The cryo-microtome can be set to cut the lenticules to a particular cut thickness $TL_{CUT}$ corresponding to a percentage P of the swollen thickness $TC_{SWELL}$ measured in act 410. Additionally, the cryo-microtome can be employed to determine the thickness $TC_{CUT}$ of the cornea at the time of cutting in act 412.

In an example scenario, the cornea is measured in act 404 to have a post-operation thickness $TC_{POST\text{-}OP}$ of 500 μm and the cornea swells to a swollen thickness $TC_{SWELL}$ of 1000 μm as measured in act 410. If the cornea does not experience any further changes in thickness after swelling in act 408, the measured thickness $TC_{CUT}$ of the cornea at the time of cutting in act 412 is 1000 μm. The cryo-microtome is set to make a series of cuts at a selected thickness $TL_{CUT}$ of 100 μm. Based on the setting for the cryo-microtome ($TL_{CUT}$=100 μm) and the thickness of the cornea measured at the time of cutting ($TC_{CUT}$=1000 μm), each lenticule is $P=(TL_{CUT}/TC_{CUT})=10\%$ of the cornea.

As described above, lenticules may provide a more general shape (e.g., a blank) that can be subsequently reshaped to form an implant that causes a desired change in refractive power. Thus, in act 418, the lenticules are reshaped with a laser to produce implants of desired shapes. Prior to act 418, however, the lenticules may experience drying, freezing, and/or other manipulation in act(s) 414, which cause the lenticules to experience additional changes in thickness. The lenticules are measured in act 416, e.g., with an OCT system, to determine the changed thickness $TL_{CHANGE}$. Act 418 can then use the measurements to account for the additional changes in thickness prior to reshaping.

For instance, in the example scenario above, a lenticule has a thickness $TL_{CUT}$ of 100 μm when cut from the cornea in act 412, but after some events 414, the lenticule may be measured in act 416 to have a changed thickness $TL_{CHANGE}$ of 75 μm. Even though there is a changed thickness $TL_{CHANGE}$, it is known that the lenticule, from the time of its cutting in act 412, is still P=10% of the cornea. The cornea in physiological hydration conditions deswells to the thickness of 500 μm as measured in act 404. Correspondingly, P=10% of the cornea will deswell to 10% of 500 μm, i.e., 50 μm. Thus, the lenticule will deswell from 75 μm as measured in act 416 to 50 μm. Accordingly, the reshaping in act 418 can take into account that the implant will deswell by a factor of 1.5. If the final implant should have a thickness of 40 μm, the reshaping in act 418 would cut the lenticule to 60 μm in thickness prior to deswelling. The deswell factor used in act 418 can be calculated as the changed thickness $TL_{CHANGE}$ of the lenticule as measured in act 416 divided by the product of the percentage P of the lenticule relative to the cornea as determined in act 412 multiplied by the thickness $TC_{POST\text{-}OP}$ of the cornea as measured in act 404.

In the example scenario above, the cornea does not experience any further changes in thickness after swelling in act 408. In other scenarios, however, the measured thickness $TC_{CUT}$ of the cornea at the time of cutting in act 412 can change from the swollen thickness $TC_{SWELL}$ measured in act 410. For instance, the thickness $TC_{CUT}$ of the cornea at the time of cutting in act 412 may be 800 μm. If the lenticules should be P=10% of the cornea, the cryo-microtome lenticules can be set to make a series of cuts separated by a selected thickness $TL_{CUT}$ of 80 μm. The acts 414, 416, 418 apply as described above. Even though the selected thickness $TL_{CUT}$ is 80 μm, the percentage P remains the same and the deswell factor in act 418 is still calculated as the changed thickness $TL_{CHANGE}$ of the lenticule as measured in act 416 divided by the product of the percentage P as determined in act 412 multiplied by the post-operation thickness $TC_{POST\text{-}OP}$ of the cornea as measured in act 404.

Figure 5:
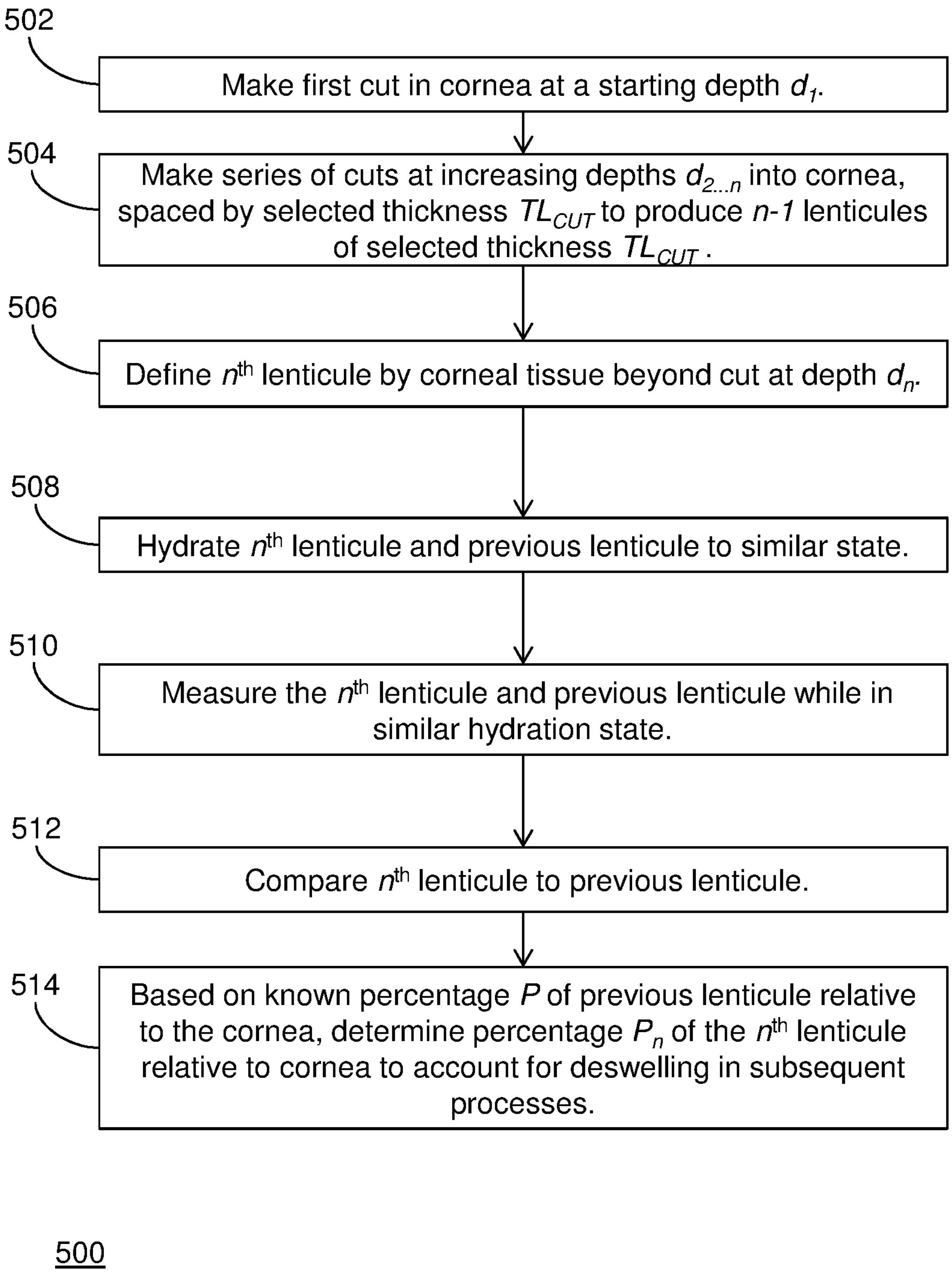
FIG. 5 illustrates an example approach for producing a plurality of lenticules from a donor cornea and accounting for deswelling associated with each lenticule, according to aspects of the present disclosure.

As described above, in the act 412, the cornea can be cut into lenticules with a cryo-microtome (or similar cutting device). Once the percentage P for the lenticules relative to the cornea has been determined (e.g., P=10%), the cryo-microtome can be set to make series of cuts that are spaced by a thickness $TL_{CUT}$ corresponding to the percentage P. FIG. 5 illustrates an example approach 500 for making the series of cuts by the cryo-microtome and determining the deswelling associated with each lenticule produced by the cuts. In act 502, the cryo-microtome makes a first cut in the cornea at a starting depth $d_1$ in act 502. The starting depth $d_1$ of the first cut may be a few microns deep into the cornea. In act 504, the cryo-microtome proceeds to make a series of cuts at increasing depths $d_{2 \ldots n}$ into the cornea, where the depths $d_{1 \ldots n}$ are spaced by the selected thickness $TL_{CUT}$. The cryo-microtome ceases the series of cuts at depth $d_n$, because the cornea is not sufficiently thick to allow the cryo-microtome to make another cut at a depth $d_{n+1}=d_n+TL_{CUT}$. The series of cuts at depths $d_{1 \ldots n}$ produce n−1 lenticules of selected thickness $TL_{CUT}$. The $n^{th}$ lenticule, however, is defined in act 506 by the remaining corneal tissue beyond the cut at the depth $d_n$. The $n^{th}$ lenticule does not have the selected thickness $TL_{CUT}$. Although one may attempt to cut the entire cornea evenly into n lenticules with the selected thickness $TL_{CUT}$, errors in cutting the n−1 lenticules and the starting depth $d_1$ of the first cut may result in a final volume of corneal tissue with less than thickness $TL_{CUT}$ for the $n^{th}$ lenticule.

Unlike the first n−1 lenticules, the percentage $P_n$ of the $n^{th}$ lenticule relative to the cornea is not immediately known. Without the percentage $P_n$, further processing of the $n^{th}$ lenticule cannot accurately account for the effect of deswelling. Thus, to determine the percentage $P_n$ of the $n^{th}$ lenticule accurately, the $n^{th}$ lenticule and the previous lenticule produced by the cuts at depths $d_{n-1}$ and $d_n$ can be hydrated in act 508 to a substantially similar state. In act 510, the $n^{th}$ lenticule and the previous lenticule can be measured, e.g., with an OCT system, while in similar hydration states. With the measurements from act 510, the size of the $n^{th}$ lenticule can be properly compared to the previous lenticule in act 512. Because the percentage P of the previous lenticule relative to the cornea is known, the percentage of the $n^{th}$ lenticule relative to the cornea can then be determined in act 514. With this percentage $P_n$, acts 414, 416, and 418 apply as described above. Specifically, the reshaping of the $n^{th}$ lenticule in act 418 can account for the deswelling that will occur during physiological hydration conditions (i.e., when the resulting implant is received by the living recipient).

The present inventors have also determined that for a given hydration state, tissue from more anterior portions of the cornea may be denser than tissue from more posterior portions of the cornea. As such, the swelling of a given volume of corneal tissue may also depend on the portion of the cornea from which the given volume of corneal tissue is taken. For instance, the given volume of corneal tissue may swell more if it is taken from a more posterior portion of the cornea. As such, embodiments can further account for the portion of the cornea from which the given volume of tissue is taken. By considering differences in swelling based on anterior/posterior regions, swollen corneal tissue can be cut more accurately to achieve an implant with a desired thickness in the living recipient. For instance, referring to FIG. 4, when the series of cuts are made at increasing depths into the cornea (e.g., from anterior cornea to posterior cornea) to produce a plurality of lenticules in act 412, the respective anterior/posterior regions from which the lenticules are cut can be recorded and subsequently used in act 418 to account for deswelling that may depend on the respective anterior/posterior regions.

Figure 6:
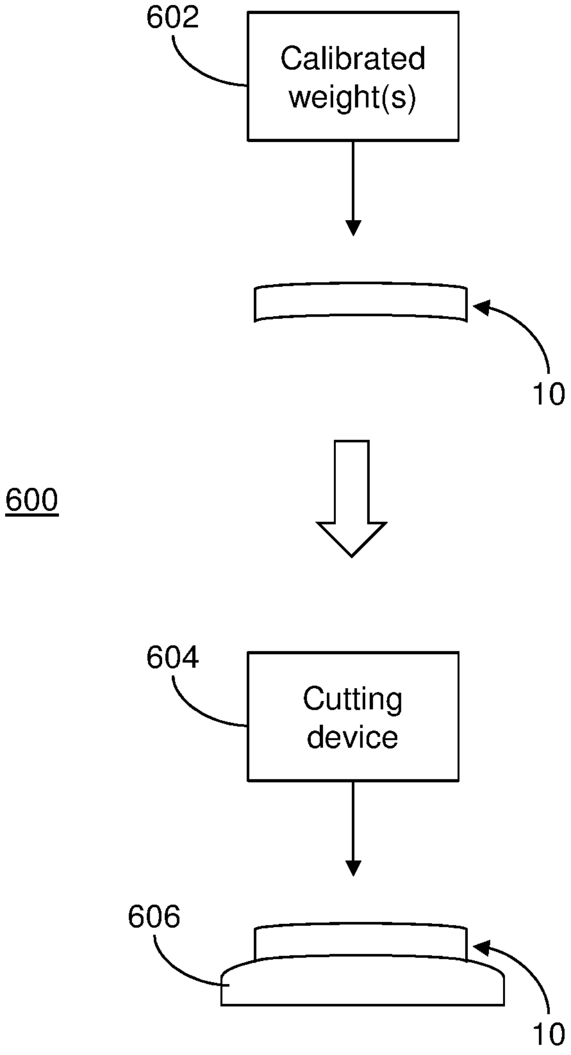
FIG. 6 illustrates an example approach for producing a corneal implant by reshaping a lenticule from a donor cornea, where the approach accounts for swelling of the lenticule, according to aspects of the present disclosure.

FIG. 6 illustrates an example approach 600 for reshaping lenticules to produce implants while accounting for any swelling. In particular, one or more calibrated weights 602 are placed on a lenticule 10 to squeeze the corneal tissue down to a thickness that corresponds more closely to the thickness it attains when it deswells in physiological hydration conditions. The calibrated weight(s) 602 are placed to apply uniform pressure across the lenticule 10, particularly to avoid folding or rolling at the periphery. The calibrated weight(s) 602 may be applied to provide varying amounts of pressure at different times and for different durations. Once the desired thickness is achieved, a cutting device 604 (e.g., a trephine) can be applied to the lenticule 10. During the cutting process, the lenticule 10 can be positioned on a device 606 (e.g., a mandrel) with a contoured surface that approximates the curvature of a cornea.

In other approaches, a donor cornea can be squeezed with pressure and frozen when the donor cornea reaches a thickness that corresponds more closely to its thickness in physiological hydration conditions.

In the embodiments above, the hydration state and corresponding aspects of corneal tissue can be evaluated via raman spectroscopy, $2^{nd}$ harmonic measurements, holography or the like.

Aspects of the embodiments above may be implemented with computer-based controllers that can execute programmed instructions stored on computer-readable storage media. For instance, such controllers can be implements to control the disclosed measurement systems and/or process signals and information from the measurement systems.

While the present disclosure has been described with reference to one or more particular embodiments, those skilled in the art will recognize that many changes may be made thereto without departing from the spirit and scope of the present disclosure. Each of these embodiments and obvious variations thereof is contemplated as falling within the spirit and scope of the invention. It is also contemplated that additional embodiments according to aspects of the present disclosure may combine any number of features from any of the embodiments described herein.

What is claimed is:

1. A method for processing corneal tissue, comprising:

receiving a corneal tissue;

placing the corneal tissue in a well defined by a first wall, wherein the first wall includes a first bottom portion that defines a bottom of the well;

adhering the corneal tissue to the first bottom portion;

filling the well with a fluid medium to keep the corneal tissue hydrated in the well;

sealing the corneal tissue and the fluid medium in the well by positioning a second wall over the first wall and coupling the second wall to the first wall, the second wall including a recess configured to extend into the well to define a chamber between the first wall and the second wall, the chamber configured to hold the corneal tissue when the well is sealed; and shaping the corneal tissue with a laser while the corneal tissue is in the well.

2. The method of claim 1, further comprising sterilizing the corneal tissue while the corneal tissue is in the well.

3. The method of claim 1, further comprising measuring the corneal tissue while the corneal tissue is in the well.

4. The method of claim 3, wherein the corneal tissue is measured with an optical coherence tomography (OCT) system, the OCT system being positioned to direct incident light to the corneal tissue in the well and to receive optical scattering from the corneal tissue in response to the incident light, the optical scattering indicating a measurement of the corneal tissue.

5. The method of claim 3, wherein the corneal tissue is measured with a second-harmonic generation (SHG) or third-harmonic generation (THG) microscopy system, the SHG or THG microscopy system including:

a light source positioned to direct incident light to the corneal tissue; and a detector positioned to receive a respective $2^{nd}$ or $3^{rd}$ harmonic light respectively from the corneal tissue in response to the incident light, the respective $2^{nd}$ or $3^{rd}$ harmonic light indicating a measurement of the corneal tissue, wherein the light source and the detector are positioned on opposite sides of the first wall and the first wall is transmissive to allow the detector to receive the respective $2^{nd}$ or $3^{rd}$ harmonic light.

6. The method of claim 5, wherein the second wall includes a second bottom portion that defines a bottom of the recess, wherein the corneal tissue is positioned between the first bottom portion and the second bottom portion when the second wall seals the well.

7. The method of claim 6, wherein a distance between the first bottom portion and the second bottom portion for receiving the corneal tissue is approximately 100 μm.

8. The method of claim 6, wherein a distance between the first bottom portion and the second bottom portion allows the corneal tissue with a thickness between approximately 10 μm and approximately 50 μm to be received.

9. The method of claim 6, wherein the corneal tissue comprises a lenticule, and wherein a distance between the first bottom portion and the second bottom portion is configured to hold the lenticule in place.

10. The method of claim 3, wherein measuring the corneal tissue while the corneal tissue is in the well comprises performing a first measurement prior to shaping the corneal tissue, and performing a second measurement subsequent to shaping the corneal tissue.

11. The method of claim 1, further comprising holding the corneal tissue in place by the first bottom portion, and wherein the first bottom portion is contoured to hold the corneal tissue in place.

12. The method of claim 11, wherein holding, by the first bottom portion, the corneal tissue in place comprises adhering the corneal tissue to the first bottom portion.

13. The method of claim 11, wherein the corneal tissue has a diameter of up to approximately 10 millimeters and the first bottom portion is configured to allow the corneal tissue to be situated along the first bottom portion without folding or rolling.

14. The method of claim 11, wherein the second wall includes a second bottom portion that defines a bottom of the recess, wherein the corneal tissue is positioned between the first bottom portion and the second bottom portion when the second wall seals the well.

15. The method of claim 14, wherein the second bottom portion is contoured to hold the corneal tissue in place.

16. The method of claim 1, wherein the first wall includes a first top portion that defines a first periphery at a top of the well, the second wall includes a second top portion that defines a second periphery at a top of the recess, and the second wall seals the well when the second top portion is coupled to the first top portion.

17. The method of claim 1, wherein the corneal tissue comprises a lenticule.

18. The method of claim 1, wherein the first bottom portion is planar.

19. The method of claim 1, wherein the first bottom portion is formed from glass.

20. The method of claim 1, wherein shaping the corneal tissue occurs prior to sealing the corneal tissue in the well.

* * * * *